US00PP26654P2

(12) United States Plant Patent
O'Byrne

(10) Patent No.: US PP26,654 P2
(45) Date of Patent: Apr. 26, 2016

(54) ***DAPHNE* PLANT NAMED 'MOONLIGHT SONATA'**

(50) Latin Name: *Daphne×burkwoodii*
Varietal Denomination: Moonlight Sonata

(71) Applicant: Ernest O'Byrne, Eugene, OR (US)

(72) Inventor: Ernest O'Byrne, Eugene, OR (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 91 days.

(21) Appl. No.: 13/998,226

(22) Filed: Oct. 11, 2013

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

(56) References Cited

PUBLICATIONS

Grows on You (http://www.growsonyou.com/photo/slideshow/275670-daphne-x-burkwoodii-moonlight-sonata); Jul. 2013.*

* cited by examiner

*Primary Examiner* — Kent L Bell
(74) *Attorney, Agent, or Firm* — C. A. Whealy

(57) ABSTRACT

A new and distinct cultivar of *Daphne* plant named 'Moonlight Sonata', characterized by its upright, outwardly spreading and mounding plant habit; moderately vigorous growth habit; freely branching habit; pale yellow and green variegated leaves; and good garden performance.

2 Drawing Sheets

Botanical designation: *Daphne×burkwoodii.*
Cultivar denomination: 'MOONLIGHT SONATA'.

BACKGROUND OF THE INVENTION

The present invention relates to a new and distinct cultivar of *Daphne* plant, botanically known as *Daphne×burkwoodii* and hereinafter referred to by the name 'Moonlight Sonata'.

The new *Daphne* plant is a naturally-occurring branch mutation of *Daphne×burkwoodii* 'Briggs Moonlight', not patented. The new *Daphne* plant was discovered and selected by the Inventor during the spring of 2003 on a single plant within a population of plants of 'Briggs Moonlight' in a controlled nursery environment in Eugene. Oreg.

Asexual reproduction of the new *Daphne* plant by softwood cuttings in a controlled greenhouse environment in Eugene. Oreg. since July, 2004 has shown that the unique features of this new *Daphne* plant are stable and reproduced true to type in successive generations of asexual reproduction.

SUMMARY OF THE INVENTION

Plants of the new *Daphne* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Moonlight Sonata'. These characteristics in combination distinguish 'Moonlight Sonata' as a new and distinct *Daphne* plant:

1. Upright, outwardly spreading and mounding plant habit.
2. Moderately vigorous growth habit.
3. Freely branching habit.
4. Pale yellow and green variegated leaves.
5. Good garden performance.

Plants of the new *Daphne* can be compared to plants of the mutation parent, 'Briggs Moonlight'. Plants of the new *Daphne* differ primarily from plants of 'Briggs Moonlight' in leaf color as leaves of plants of 'Briggs Moonlight' have narrower green-colored margins.

Plants of the new *Daphne* can be compared to plants of the *Daphne×burkwoodii* 'Somerset', not patented. In side-by-side comparisons conducted in Grand Haven, Mich., plants of the new *Daphne* differed primarily from plants of 'Somerset' in leaf color as leaves of plants of 'Somerset' were solid green in color.

BRIEF DESCRIPTION OF THE PHOTOGRAPHS

The accompanying colored photographs illustrate the overall appearance of the new *Daphne* plant showing the colors as true as it is reasonably possible to obtain in colored reproductions of this type. Colors in the photographs may differ slightly from the color values cited in the detailed botanical description which accurately describe the colors of the new *Daphne* plant.

The photograph on the first sheet is a side perspective view of a typical plant of 'Moonlight Sonata' grown in an outdoor nursery.

The photograph on the second sheet is a close-up view of a typical plant of 'Moonlight Sonata'.

DETAILED BOTANICAL DESCRIPTION

The aforementioned photographs and following observations, measurements and values describe plants grown during the summer in ground beds in an outdoor nursery in Grand Haven, Mich. and under cultural practices which closely approximate commercial *Daphne* production. Plants used for the photographs and description were five years old. In the following detailed description, color references are made to The Royal Horticultural Society Colour Chart, 1995 Edition, except where general terms of ordinary dictionary significance are used.

Botanical classification: *Daphne×burkwoodii* 'Moonlight Sonata'.

Parentage: Naturally-occurring branch mutation of *Daphne× burkwoodii* 'Briggs Moonlight', not patented.

Propagation:

*Type*.—By softwood cuttings.

*Time to initiate roots, summer*.—About one month at temperatures about 24° C.

*Time to produce a rooted young plant, summer*.—About eight months at temperatures about 24°.

*Root description*.—Fine to thick; somewhat fleshy and fibrous; brown and creamy white in color.

*Rooting habit*.—Freely branching; dense.

Plant description:

*Plant form and growth habit*.—Perennial shrub; upright, outwardly spreading and mounding plant habit; moderately vigorous growth habit; freely branching habit with about 42 lateral branches developing per plant.

*Plant height*.—About 75 cm.

*Plant diameter* (*area of spread*).—About 125 cm.

Lateral branch description:

*Length*.—About 12 cm.

*Diameter*.—About 3.5 mm.

*Internode length*.—About 2 mm.

*Aspect*.—Erect to outwardly spreading.

*Strength*.—Strong, flexible.

*Texture*.—Smooth, glabrous.

*Color, young*.—Close to 160B.

*Color, mature*.—Close to 164A to 164B.

Leaf description:

*Arrangement*.—Whorled; simple; sessile.

*Length*.—About 3.5 cm.

*Width*.—About 8 mm.

*Shape*.—Lanceolate to slightly oblong to obovate.

*Apex*.—Acute to obtuse.

*Base*.—Narrowly cuneate.

*Margin*.—Entire.

*Texture, upper and lower surfaces*.—Smooth, glabrous; thick.

*Venation pattern*.—Pinnate.

*Color*.—Developing leaves, upper surface: Center, close to 10D; margins, close to 138A to 138D. Developing leaves, lower surface: Center, close to 192B to 192D; margins, close to 138A to 138B. Fully expanded leaves, upper surface: Center, close to 10C; margins, close to 139B to 139C; venation, similar to lamina colors. Fully expanded leaves, lower surface: Center, close to 192B to 192D; margins, close to 139B to 139C; venation, similar to lamina colors.

Flower description: Flower initiation and development have not been observed on plants of the new *Daphne*.

Garden performance: Plants of the new *Daphne* have been observed to have excellent garden performance and to tolerate high light, rain, wind and temperatures ranging from about −25° C. to about 40° C.

Pathogen & pest resistance: Plants of the new *Daphne* have not been observed to be resistant to pathogens and pests common to *Daphne* plants.

It is claimed:

1. A new and distinct *Daphne* plant named 'Moonlight Sonata' as illustrated and described.

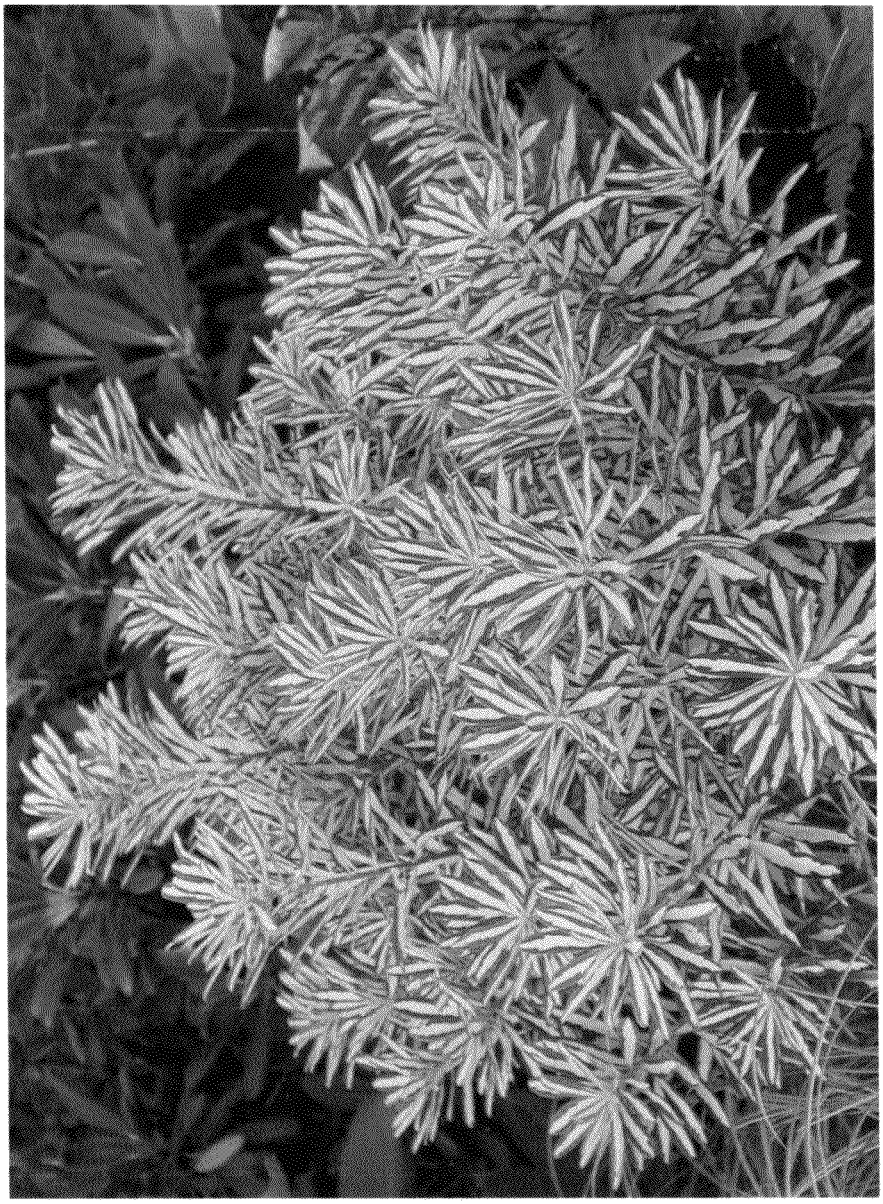

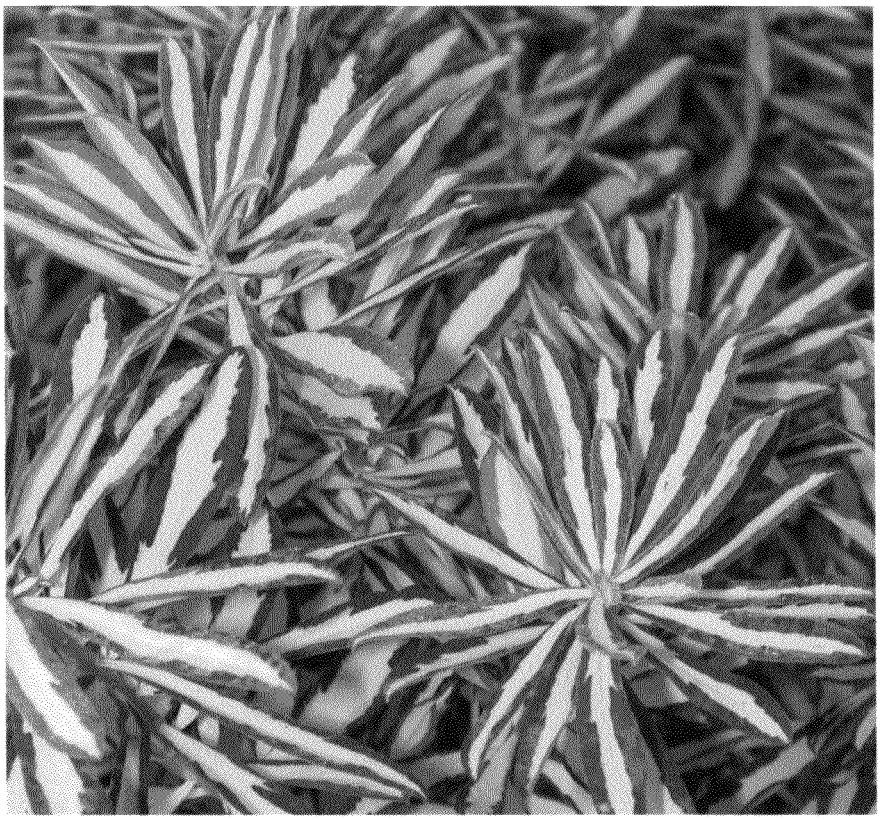

* * * * *